United States Patent
Izawa et al.

(10) Patent No.: US 10,125,109 B2
(45) Date of Patent: Nov. 13, 2018

(54) METHOD FOR PRODUCING FURAN COMPOUND AND FURFURAL COMPOSITION

(71) Applicant: Mitsubishi Chemical Corporation, Chiyoda-ku (JP)

(72) Inventors: Yusuke Izawa, Mie (JP); Hideto Tsuji, Kanagawa (JP); Yosuke Suzuki, Mie (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 0 days.

(21) Appl. No.: 15/712,844

(22) Filed: Sep. 22, 2017

(65) Prior Publication Data

US 2018/0009774 A1 Jan. 11, 2018

Related U.S. Application Data

(63) Continuation of application No. PCT/JP2016/059514, filed on Mar. 24, 2016.

(30) Foreign Application Priority Data

Mar. 27, 2015 (JP) .................................. 2015-067199

(51) Int. Cl.
| | |
|---|---|
| *C07D 307/02* | (2006.01) |
| *C07D 307/36* | (2006.01) |
| *C07D 307/48* | (2006.01) |
| *B01J 23/58* | (2006.01) |
| *C07B 61/00* | (2006.01) |

(52) U.S. Cl.
CPC ......... *C07D 307/36* (2013.01); *C07D 307/48* (2013.01); *B01J 23/58* (2013.01); *C07B 61/00* (2013.01)

(58) Field of Classification Search
CPC .. C07D 307/36; C07D 307/48; C07D 307/02; B01J 23/58
USPC ........................................................ 549/505
See application file for complete search history.

(56) References Cited

FOREIGN PATENT DOCUMENTS

| | | |
|---|---|---|
| JP | 2009-132656 | 6/2009 |
| JP | 2009-149634 | 7/2009 |
| JP | 2013-159594 A | 8/2013 |
| JP | 2014-12663 | 1/2014 |
| JP | 2014012663 | * 1/2014 |
| WO | WO 2009/069714 A1 | 6/2009 |
| WO | WO 2015/170718 A1 | 11/2015 |

OTHER PUBLICATIONS

International Search Report dated May 31, 2016 in PCT/JP2016/059514, filed on Mar. 24, 2016 (with English Translation).
Written Opinion dated May 31, 2016 in PCT/JP2016/059514, filed on Mar. 24, 2016.
Extended European Search Report dated Dec. 19, 2017 in European Patent Application No. 16772587.8, 11 pages.
Yao-Bing Huang, et al., "Heterogeneous Palladium Catalysts for Decarbonylation of Biomass-Derived Molecules under Mild Conditions", ChemSusChem, vol. 6 No. 8, XP55429956, Jul. 2, 2013, pp. 1348-1351.
"Aldrich catalog 2005-2006", XP002776208,2005, p. 1280.
James G. Stevens, et al., "Real-Time Product Switching Using a Twin Catalyst System for the Hydrogenation of Furfural in Supercritical $CO_2$ ", Angewandte Chemie International Edition, vol. 49 No. 47, XP 55430004, Oct. 6, 2010, pp. 8856-8859.
Jungho Jae, et al., "Production of Dimethylfuran from Hydroxymethylfurfural through Catalytic Transfer Hydrogenation with Ruthenium Supported on Carbon", ChemSusChem, vol. 6 No. 7, XP55153258, Jul. 10, 2013, pp. 1158-1162.
Frank M. A. Geilen, et al., "Highly Selective Decarbonylation of 5-(Hydroxymethyl) furfural in the Presence of Compressed carbon Dioxide", Angewandte Chemie International Edition, vol. 50 No. 30, XP55430038, Jun. 9, 2011, pp. 6831-6834.

* cited by examiner

*Primary Examiner* — Taylor V Oh
(74) *Attorney, Agent, or Firm* — Oblon, McClelland, Maier & Neustadt, L.L.P.

(57) ABSTRACT

The present invention is aimed to provide an industrially advantageous method for producing a furan compound, in which a furan compound can be efficiently obtained in a high selectivity from a furfural compound. The present invention is concerned with a method for producing a furan compound including feeding, as a raw material, a furfural composition containing a furfural compound into a reactor and subjecting to a decarbonylation reaction in the presence of a catalyst to obtain a furan compound as a product, wherein a furfural dimer concentration in the furfural composition is 1,000 ppm by weight or less, and a peroxide value in the furfural composition is 0.01 mEq/kg or more and 1.0 mEq/kg or less.

4 Claims, No Drawings

METHOD FOR PRODUCING FURAN COMPOUND AND FURFURAL COMPOSITION

TECHNICAL FIELD

The present invention relates to a method for producing a furan compound wherein a furan compound is produced through a decarbonylation reaction from a furfural compound.

BACKGROUND ART

There has hitherto been developed a method of producing a chemical, for example, ethanol, succinic acid, 1,4-butanediol, etc., from a biomass resource by means of fermentation. In the case of using a nonedible biomass resource, a furfural compound which is formed from a hemicellulose or the like becomes a fermentation-inhibiting component. For that reason, conventionally, it was general that the furfural compound is removed as an impurity. However, from the viewpoint of efficiently using the biomass resource, a technique of producing a chemical from a furfural which is formed from a hemicellulose is considered to be necessary.

A technique of extracting a furfural compound from a biomass resource has been studied from long ago. The furfural compound is also industrially produced as a raw material of a furan resin or the like. As other chemicals, for example, it may be considered to use the furfural compound as a raw material for producing a furan compound (tetrahydrofuran) therefrom. However, as for the furfural compound to be used as a raw material for producing a furan resin, in the production of such a chemical, a furfural compound having a higher purity is required.

There has hitherto been known a method of producing furan through a decarbonylation reaction from furfural in the presence of a catalyst (for example, Patent Literature 1). In addition, as a method of stably converting furfural into furan to produce the furan in a high efficiency, for example, Patent Literature 2 discloses a method in which in producing furan from furfural through a gas phase flow reaction, impurities which cause a lowering of the catalytic activity in crude furfural, specifically a sulfur component and so on are previously removed by means of distillation, adsorption separation, or the like, to obtain a raw material furfural having an acid value of a fixed value or less, which is then subjected to a decarbonylation reaction step.

In addition, in producing furan from furfural, as a method of purifying the furfural as a raw material in advance, Patent Literature 3 discloses a method in which after carrying out the treatment with a base in advance, distillation purification is performed.

BACKGROUND ART LITERATURE

Patent Literature

Patent Literature 1: JP-A-2009-149634
Patent Literature 2: JP-A-2009-132656
Patent Literature 3: JP-A-2014-12663

SUMMARY OF INVENTION

Technical Problem

According to the purification method of furfural as disclosed in Patent Literature 3, it is possible to obtain a furfural composition which is suitable for production of a furan compound having reduced impurities. However, according to this method, even in the purified furfural composition having a relatively high purity, the catalytic activity of a catalyst to be used for the decarbonylation reaction was lowered, so that a conversion of the furfural compound in the furfural composition or the yield of the obtained furan compound was insufficient.

In view of the above-described problems, the present invention has been made, and an object thereof is to provide an industrially advantageous method for producing a furan compound, in which in obtaining a furan compound from a furfural composition containing a furfural compound through a decarbonylation reaction, not only the decarbonylation reaction of the furfural compound can be advanced in a high conversion, but also the desired furan compound can be efficiently obtained in a high selectivity.

Solution to Problem

In order to solve the above-described problem, the present inventors made extensive and intensive investigations. As a result, they discovered that there are existent some substances which cannot be thoroughly removed by the purification of furfural as described in Patent Literature 3 and so on. Then, in the case of using the foregoing furfural as a raw material of a furan compound, it has been found that there is correlation between a conversion of the furfural by the decarbonylation reaction and a selectivity of the desired furan compound due to the existence of such a substance. Examples of such a substance include a furfural dimer and a peroxide in the furfural composition, and it has been found that by controlling a concentration of the furfural dimer and a peroxide value to certain values, the above-described problem can be solved, leading to accomplishment of the present invention.

Specifically, the gist of the present invention resides in the following [1] to [6].

[1] A method for producing a furan compound containing feeding, as a raw material, a furfural composition containing a furfural compound into a reactor and subjecting to a decarbonylation reaction in the presence of a catalyst to obtain a furan compound as a product, wherein a furfural dimer concentration in the furfural composition is 1,000 ppm by weight or less, and a peroxide value in the furfural composition is 0.01 mEq/kg or more and 0.90 mEq/kg or less.

[2] The method for producing a furan compound according to the above [1], wherein concentration of a compound containing nitrogen in the furfural composition as a raw material is 0.1 ppm by weight or more and 50 ppm by weight or less.

[3] The method for producing a furan compound according to the above [1] or [2], wherein a concentration of the furfural compound in the furfural composition as a raw material is 99.00% by weight to 99.97% by weight.

[4] The method for producing a furan compound according to any one of the above [1] to [3], wherein a 2-acetylfuran concentration in the furfural composition as a raw material is 120 ppm by weight or more and 1,000 ppm by weight or less.

[5] A furfural composition having
a concentration of a furfural compound of 99.00% by weight to 99.97% by weight,
a concentration of a furfural dimer of 1,000 ppm by weight or less, and a peroxide value of 0.01 mEq/kg or more and 0.90 mEq/kg or less.

[6] The furfural composition according to the above [5], wherein a 2-acetylfuran concentration in the furfural composition is 120 ppm by weight or more and 1,000 ppm by weight or less.

Effects of Invention

In accordance with the present invention, it is possible to stably obtain a furan compound in a high yield from a furfural composition containing a furfural compound.

DESCRIPTION OF EMBODIMENTS

Although embodiments of the present invention are hereunder described in detail, it should be construed that the present invention is by no means limited to the following embodiments and can be variously modified and carried out within the scope of the gist thereof.

<Furfural Compound>

The furfural compound which is contained in the furfural composition as a raw material to be used in the production method of a furan compound according to the present invention and in the furfural composition according to the present invention refers to a compound represented by the following general formula (1).

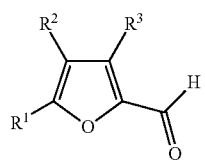

(1)

In the general formula (1), the substituents $R^1$, $R^2$, and $R^3$ may be the same as or different from each other. As for the kinds of the substituents $R^1$, $R^2$, and $R^3$, examples thereof include a hydrogen atom, an aliphatic hydrocarbon group which may have a functional group, an aromatic hydrocarbon group which may have a functional group, a hydroxyl group, an acetyl group, and an aldehyde group. Among these, $R^1$, $R^2$, and $R^3$ are each preferably a hydrogen atom, a hydroxyl group, or a methyl group, and more preferably a hydrogen atom or a hydroxyl group.

Specifically, preferred examples of the furfural compound include furfural (2-furancarboxyaldehyde), hydroxymethylfurfural, 2-methylfurfural, 3-methylfurfural, furfuryl dialdehyde, and 5-methylfurfural. Above all, furfural (2-furancarboxyaldehyde) in which all of $R^1$, $R^2$, and $R^3$ in the general formula (1) are a hydrogen atom is most preferred.

<Furfural Composition>

The furfural composition according to the present invention and the furfural composition as a raw material in the production method of a furan compound can be obtained from crude furfural. As the crude furfural, in general, one obtained by a method in which a plant (nonedible biomass resource) containing a hemicellulose component, such as corncob, bagasse, sawdust of wood, etc., or the like is heated in the presence of an acid, such as dilute sulfuric acid, etc., to generate furfural and water, and a mixture containing furfural and water as thus generated is then subjected to a dehydration treatment can be used. However, the crude furfural is not always limited to one obtained by this method. For example, a method in which a reactor for furfural production is provided in reactive distillation, and a mixture of furfural and water is continuously discharged, as described in WO2013/102027; a method in which furfural is continuously extracted with an organic solvent from an aqueous phase, as described in WO2012/115706; and so on can also be adopted. Although a concentration of the furfural compound in the crude furfural is not particularly limited, it is typically 90% by weight or more and 98.7% by weight or less, preferably 95% by weight or more and 98.5% by weight or less, more preferably 97% by weight or more and 98.3% by weight or less, and most preferably 97.5% by weight or more and 98.0% by weight or less.

The furfural composition according to the present invention and the furfural composition as a raw material in the production method of a furan compound can be obtained from the above-described crude furfural. In addition, for example, in the case where the furfural compound is furfural, in obtaining the furfural composition from the crude furfural, it is preferred that after bringing the crude furfural into contact with an anion exchange resin and/or a basic compound, a compound having a higher boiling point than furfural, or a compound having a lower boiling point than furfural, is separated and removed by means of distillation.

Although the above-described anion exchange resin is not particularly limited, a weakly basic anion exchange resin is preferable. Specifically, examples thereof include weakly basic anion exchange resins, such as an acrylic type, a styrene-based polyamide type, etc.; and strongly basic anion exchange resins having a trimethylammonium group, a dimethylethanolammonium group, or the like.

Although the above-described basic compound is not particularly limited, examples thereof include a basic inorganic compound, a basic organic compound, and the like.

Specific examples of the basic inorganic compound include hydroxides of an alkali metal, such as lithium hydroxide, sodium hydroxide, potassium hydroxide, etc.; hydroxides of an alkaline earth metal, such as barium hydroxide, calcium hydroxide, etc.; and carbonates, such as sodium carbonate, potassium carbonate, sodium bicarbonate, etc.

Specific examples of the basic organic compound include methylamine, etheramine, ethylamine, trimethylamine, triethylamine, tributylamine, triethanolamine, N,N-diisopropylethylamine, piperidine, piperazine, morpholine, quinuclidine, pyridine, 1,4-diazabicyclooctane, 4-dimethylaminopyridine, ethylenediamine, tetramethylethylenediamine, hexamethylenediamine, aniline, catecholamine, phenethylamine, 1,8-bis(dimethylamino)naphthalene (proton sponge), and the like.

Although the amount of the anion exchange resin and/or the basic compound to be brought into contact with the crude furfural is not particularly limited, it is preferably 0.005 to 1 wt %, more preferably 0.01 to 0.5 wt %, and still more preferably 0.03 to 0.3 wt % relative to the amount of the crude furfural.

A mode of the contact of the anion exchange resin and/or the basic compound with the crude furfural as a raw material is not particularly limited, and any means of a fixed bed flow type or a batch type, or the like may be taken. Although a contact temperature in the fixed bed flow type is not particularly limited, it is preferably in the range of from 10° C. to 90° C., more preferably in the range of from 15° C. to 70° C., and especially preferably in the range of from 20° C. to 60° C. Although a retention time is not particularly limited, it is preferably 0.05 hours to 10 hours, more preferably 0.1 hours to 5 hours, and still more preferably 0.5 hours to 2 hours. Although a contact temperature in the batch type is not particularly limited, it is preferably in the range of from 10° C. to 90° C., more preferably in the range of from 15° C. to 70° C., and especially preferably in the range of from 20° C. to 50° C. Although a contact time is not particularly limited, it is preferably 0.5 hours to 20 hours, more preferably 0.5 hours to 10 hours, and still more preferably 1 hour to 5 hours.

It is preferred that as described above, the crude furfural is brought into contact with the anion exchange resin and/or the basic compound and then distilled with using a distillation column, thereby removing a compound having a higher boiling point than furfural or a compound having a lower boiling point than furfural. However, a mode of the distillation is not particularly limited, and any of batch or continuous distillation may be used. As for a structure of the distillation column, any of a plate column using a sieve tray or bubble cap tray, etc. or a packed column using structured packings or random packings may be adopted.

It is preferred to obtain the furfural composition according to the present invention and the furfural composition as a raw material in the production method of a furan compound in such a manner that after the above-described crude furfural is brought into contact with the anion exchange resin and/or the basic compound, a compound having a higher boiling point than furfural or a compound having a lower boiling point than furfural is removed by means of distillation. As for a reason for this, it may be estimated that due to the contact of the crude furfural with the anion exchange resin and/or the basic compound, cationic polymerization to be caused by heating when the crude furfural is distilled in a purification step of the latter stage is relieved, and the generation of a solid material or the like in a distillation step can be reduced.

As the step of performing this distillation of the crude furfural, a distillation method including the following steps (a) and (b) is preferred.

(a) A step of distilling the crude furfural obtained after bringing the crude furfural into contact with the anion exchange resin and/or the basic compound by a distillation column, thereby removing a compound having a higher boiling point than furfural (b) A step of distilling the crude furfural obtained from the above-described (a), from which a compound having a higher boiling point than furfural has been removed, by a distillation column, thereby removing a compound having a lower boiling point than furfural Although a column top pressure within the distillation column in the step (a) is not particularly limited, it is preferably 0.12 to 28.2 kPa, more preferably 0.5 to 20.5 kPa, and still more preferably from 0.8 to 15.5 kPa. A column bottom temperature of the distillation column in the step (a) is preferably 60 to 125° C. Although a proportion of the compound having a higher boiling point than furfural, which is to be removed in the step (a), is not particularly limited, it is typically 30% by weight or more, preferably 50% by weight or more, more preferably 75% by weight or more, and still more preferably 90% by weight or more on the basis (100% by weight) of a total weight of compounds having a high boiling point, which are contained in the crude furfural. Although a reflux ratio is arbitrary, the reflux ratio is preferably 0.01 or more and 100 or less, more preferably 0.1 or more and 50 or less, and especially preferably 0.2 or more and 20 or less.

A column top pressure within the distillation column in the step (b) is preferably 0.12 to 300 kPa, more preferably 0.5 to 200 kPa, and still more preferably 0.8 to 100 kPa. In the step (b), a proportion of the compound having a lower boiling point than furfural, which is to be removed from the crude furfural, is typically 30% by weight or more, preferably 50% by weight or more, more preferably 75% by weight or more, and still more preferably 90% by weight or more on the basis (100% by weight) of a total weight of compounds having a low boiling point, which are contained in the crude furfural. Although a reflux ratio is arbitrary, the reflux ratio is preferably 0.1 or more and 200 or less, more preferably 0.5 or more and 100 or less, and especially preferably 1 or more and 70 or less.

As the compound having a higher boiling point than furfural, in general, compounds having a boiling point higher by at least 5° C. than the boiling point of furfural at atmospheric pressure are exemplified. Examples thereof include compounds, such as furfuryl alcohol having a boiling point of 170° C., 2-acetylfuran having a boiling point of 173° C., 2-furancarbonyl chloride having a boiling point of 173 to 174° C., 5-methylfurfural having a boiling point of 187° C., furyl methyl ketone, etc., relative to furfural having a boiling point of 162° C. at atmospheric pressure. As for the furfural dimer having a boiling point higher than 250° C., its amount can also be reduced by means of distillation.

As the compound having a lower boiling point than furfural, in general, compounds having a boiling point lower by at least 5° C. than the boiling point of furfural at atmospheric pressure are exemplified. Examples thereof include 2,3-dihydrofuran having a boiling point of 54 to 55° C., 2-methylfuran having a boiling point of 63 to 66° C., formic acid having a boiling point of 100 to 102° C., acetic acid having a boiling point of 118 to 120° C., 3-penten-2-one having a boiling point of 121 to 124° C., and the like, relative to furfural having a boiling point of 162° C. at atmospheric pressure.

In both of the steps (a) and (b), the number of theoretical plate is in the range of from 1 to 50 plates, preferably from 3 to 40 plates, and more preferably 5 to 30 plates.

In both of the steps (a) and (b), although a feed temperature of the crude furfural into the distillation column is not particularly limited, it is preferably −20 to 150° C., more preferably 0 to 130° C., and still more preferably 10 to 120° C.

In the step (a), it is preferred that the crude furfural from which the compound having a higher boiling point than furfural has been removed is discharged from the column top of the foregoing distillation column. This crude furfural discharged from the column top may be fed directly into the distillation column in the step (b); or before a part or the whole of the crude furfural discharged from the column top in the step (a) is fed into the step (b), it may be subjected to a general purification treatment, such as another distillation, extraction, etc., and then fed into the distillation column in the step (b). From the viewpoint of economy, it is preferred that the crude furfural discharged from the column top in the step (a) is fed directly into the distillation column in the step (b) without performing any treatment.

In the step (b), in the case of obtaining a final purified product, namely the furfural composition as a raw material in the production method of a furan compound according to the present invention and the furfural composition according to the present invention, from the distillation column, it is preferably discharged from a sidestream portion of the distillation column in the step (b). Although this sidestream may be either gas discharge or liquid discharge, from the viewpoint of energy costs, liquid discharge is more preferred. A sidestream discharge position is preferably located in an upper part than the feed plate of the crude furfural in the step (a) to be fed into the distillation column in the step (b). Furthermore, in a height direction of the distillation column, it is preferred to discharge the sidestream from an upper position by more than 50% of the height of the distillation column, for example, a position of 50% to 90% of the theoretical plates from the column bottom of the distillation column relative to the theoretical plates of the distillation column. In particular, it is desired that a gap between the feed plate of the crude furfural and the sidestream discharge position is 1 plate or more, and preferably 2 plates or more, for example 1 to 10 plates in terms of the theoretical plate. It is to be noted that the number of theoretical plate from the column top portion to the sidestream discharge position is preferably 1 plate or more and 50 plates or less, more preferably 2 plates or more and 20 plates or less, and especially preferably 3 plates or more and 10 plates or less.

The furfural composition according to the present invention and the furfural composition as a raw material in the production method of a furan compound can be obtained in such a manner that after bringing the above-described crude furfural into contact with the anion exchange resin and/or the basic compound, the compound having a higher boiling point than furfural is first removed by means of distillation in the step (a), and subsequently, the crude furfural obtained in the step (a) is subjected to the step (b), thereby removing the compound having a lower boiling point than furfural by means of distillation. By performing the distillation in such procedures, a furfural composition having a concentration of furfural dimer of 1,000 ppm by weight or less and a peroxide value of 0.01 mEq/kg or more and 0.90 mEq/kg or less can be obtained. This furfural composition suppresses the deterioration of a catalyst of the decarbonylation reaction, thereby enabling the decarbonylation reaction of the furfural compound to be advanced in a high conversion. The matter that the above-described furfural composition is obtained according to this distillation resides in the following reason. That is, on the occasion of paying attention to the furfural dimer or peroxide in the crude furfural, when a part or the whole of the peroxide contained in the discharged liquid from the column top in the step (a) is heated in the step (b), it is converted into a peroxide having a higher boiling point than furfural and concentrated in the column bottom. Then, when the peroxide having a higher boiling point than furfural is separated from furfural in the step (a) and furthermore, in the step (b), the peroxide whose boiling point has been made higher is discharged from the column bottom; the compound having a lower boiling point than furfural is discharged from the column top; and the furfural is discharged from the sidestream, the furfural composition in which the peroxide value is adjusted to 0.01 mEq/kg or more and 0.90 mEq/kg or less can be obtained.

The furfural composition and the production method of a furan compound according to the present invention are characterized in that a concentration of the furfural dimer, specifically, 5-(2-furanylcarbonyl)-2-furancarboxyaldehyde and/or bis-2-furylethanedione, which is contained in the furfural composition as a raw material is 1,000 ppm by weight or less.

When this furfural dimer concentration is too high, in producing a furan compound using the furfural composition as a raw material through the decarbonylation reaction, the yield of the desired furan compound is lowered, and the purity of the obtained furan compound is lowered, too.

In the furfural composition and the production method of a furan compound according to the present invention, the concentration of the furfural dimer contained in the furfural composition is preferably 0.1 ppm by weight or more, more preferably 0.2 ppm by weight or more, still more preferably 0.3 ppm by weight or more, and especially preferably 0.5 ppm by weight or more. Meanwhile, this concentration is preferably 1,000 ppm by weight or less, more preferably 500 ppm by weight or less, still more preferably 350 ppm by weight or less, and yet still more preferably 100 ppm by weight or less.

Although a reason why the furfural dimer concentration in the furfural composition influences the yield of the furan compound obtained through the decarbonylation reaction of the furfural compound is not always elucidated yet, the following reasons may be conjectured. Namely, it may be considered that in the decarbonylation reaction of the furfural compound, the furfural dimer in the furfural composition as a raw material is liable to bond to a catalyst metal species, etc. of the decarbonylation reaction catalyst and cover an active site, thereby inhibiting the decarbonylation reaction of the furfural compound. It may be conjectured that the higher this concentration, the more increased the reaction inhibition is. In addition, it may be considered that the furfural compound is high in reactivity, the furfural compounds are polymerized each other on the catalyst, and the resulting polymer causes coking of the catalyst, thereby inhibiting the decarbonylation reaction. It may be conjectured that when the amount of a polymerization precursor, such as the furfural dimer, etc., increases, the coking of the catalyst is promoted, resulting in a lowering of the reaction yield.

In addition, the furfural composition and the production method of a furan compound according to the present invention are characterized in that a peroxide value contained in the furfural composition is 0.01 mEq/kg or more and 0.90 mEq/kg or less. When this peroxide value is too high, in producing a furan compound using the furfural composition as a raw material through the decarbonylation reaction, the yield of the desired furan compound is lowered, and the purity of the obtained furan compound is lowered, too. When the peroxide value is too low, purification costs increase.

In the furfural composition and the production method of a furan compound according to the present invention, the peroxide is a compound having, as a functional group, a peroxide structure or a peroxycarboxylic acid structure. Specifically, examples thereof include inorganic compounds, such as hydrogen peroxide, etc.; peroxycarboxylic acids, such as peracetic acid, perpropionic acid, per-furan carboxylic acid, etc.; cyclic peroxides, such as 1,2-dioxin, dimethyldioxirane, acetone peroxide, etc.; and the like.

In the furfural composition and the production method of a furan compound according to the present invention, the peroxide value contained in the furfural composition is 0.01 mEq/kg or more, preferably 0.05 mEq/kg or more, more preferably 0.1 mEq/kg or more, and still more preferably 0.2 mEq/kg or more. Meanwhile, this peroxide value is 0.90 mEq/kg or less, preferably 0.7 mEq/kg or less, and more preferably 0.35 mEq/kg or less.

Although a reason why the peroxide value in the furfural composition influences the yield of the furan compound obtained through the decarbonylation reaction of the furfural compound is not always elucidated yet, the following reasons may be conjectured. Namely, it may be considered that in the decarbonylation reaction of the furfural compound, the peroxide in the furfural composition as a raw material oxidizes a catalyst metal species of the decarbonylation reaction catalyst and deactivates it, thereby inhibiting the decarbonylation reaction of the furfural compound, and it may be conjectured that the higher this concentration, the more increased the degree of catalyst degradation is. In addition, it may be considered that the furfural compound is high in reactivity, the furfural compounds are polymerized each other on the catalyst, and the resulting polymer causes coking of the catalyst, thereby inhibiting the decarbonylation reaction. It may be conjectured that when a polymerization initiating substance, such as a peroxide, is present, the coking of the catalyst is promoted, resulting in a lowering of the reaction yield.

In the furfural composition and the production method of a furan compound according to the present invention, it is preferred that a compound containing nitrogen is contained in the furfural composition. When a concentration of this compound containing nitrogen is too high, in producing a furan compound using the furfural composition as a raw material through the decarbonylation reaction, the catalyst degradation is caused, and the yield of the desired furan compound is lowered. When the concentration of the compound containing nitrogen is too low, the polymerization to be caused due to a trace acidic component in the furfural composition cannot be controlled, thereby causing coking of the catalyst or contamination of the process.

The concentration of the compound containing nitrogen which is contained in the furfural composition is preferably 0.1 ppm by weight or more, more preferably 0.3 ppm by weight or more, still more preferably 0.5 ppm by weight or more, and especially preferably 0.8 ppm by weight or more as expressed in terms of a nitrogen atom. Meanwhile, this concentration is preferably 50 ppm by weight or less, more preferably 10 ppm by weight or less, still more preferably 5 ppm by weight or less, and especially preferably 3 ppm by weight or less.

Additionally, in addition to the above-described steps (a) and (b), it is more preferred to include the following step (c).

(c) A step of distilling the compound having a higher boiling point than furfural as separated in the step (a) by a distillation column, thereby separating and recovering furfural In the above-described step (c), a trace amount of furfural contained in the liquid containing a high-boiling component as separated in the step (a) is separated and recovered. As for the treatment of the distillation column to be used, any of a batch or continuous distillation may be used. As for a mode of the distillation column, any of a plate column using a sieve tray or bubble cap tray, etc. or a packed column using structured packings or random packings may be adopted. Although a distillation condition is not particularly limited, the number of theoretical plate is preferably in the range of from 1 to 50 plates, more preferably from 3 to 30 plates, and still more preferably 5 to 20 plates. A column top pressure within the distillation column is preferably 0.12 to 28.2 kPa, more preferably 0.5 to 20.5 kPa, and still more preferably from 0.8 to 15.5 kPa.

The furfural composition as a raw material in the production method of a furan compound and the furfural composition according to the present invention each contain the above-described furfural compound as a main component. A concentration of the furfural compound contained as the main component in the furfural composition is preferably 99.00% by weight or more, and more preferably 99.20% by weight or more. Meanwhile, this concentration is preferably 99.97% by weight or less, more preferably 99.95% by weight or less, and still more preferably 99.93% by weight or less. When this concentration becomes low, there is a tendency that the decarbonylation reaction yield is lowered, and the purity of the furan compound is lowered, too, whereas when the purity is too high, there is a concern that in obtaining the furfural composition from a biomass resource, the purification costs become high.

As for a method of controlling the furfural dimer concentration in the furfural composition and the furfural composition as a raw material in the production method of a furan compound according to the present invention, in addition to a method in which before the furfural composition is fed into a reactor of the decarbonylation reaction, as described above, the furfural dimer is previously separated from the crude furfural or the furfural composition by using a distillation column, thereby reducing the concentration of the furfural dimer in the furfural composition, it is also possible to control the furfural dimer concentration by the following methods. For example, a method in which the furfural dimer in the furfural composition is converted into an another substance by using a catalyst different from the catalyst of the decarbonylation reaction to be used in producing the furan compound of the present invention, thereby reducing the furfural dimer concentration; a method in which the furfural composition is extracted and separated, thereby reducing the concentration of the furfural dimer; a method in which the furfural composition is diluted with a furfural composition having a low furfural dimer concentration; and so on are also exemplified as preferred methods. These methods may be performed either alone or in combination of two or more thereof. It is to be noted that among these, a method in which before the furfural composition is fed into a reactor of the decarbonylation reaction, as described above, the furfural or the furfural composition is previously distilled by using a distillation column, thereby separating the furfural dimer is more preferred.

As for a method of controlling the peroxide value in the furfural composition and the furfural composition as a raw material in the production method of a furan compound according to the present invention, in addition to a method in which before the furfural composition is fed into a reactor of the decarbonylation reaction, as described above, in previously distilling the crude furfural by using a distillation column, a peroxide is separated from the crude furfural or the furfural composition, thereby reducing the peroxide value, it is also possible to control the peroxide value by the following methods. For example, a method in which the peroxide is converted into an another substance by using a catalyst different from the catalyst of the decarbonylation reaction to be used in producing the furan compound of the present invention, thereby reducing the peroxide value; a method in which the furfural composition is extracted and separated, thereby reducing the peroxide value; a method in which the furfural composition is diluted with a furfural composition having a low peroxide value; and so on are also exemplified as preferred methods. These methods may be performed either alone or in combination of two or more thereof. It is to be noted that among these, a method in which before the furfural composition is fed into a reactor of the decarbonylation reaction, the furfural composition is previously distilled by using a distillation column, thereby distilling and separating a peroxide; and a method in which the furfural composition is allowed to pass through a solid catalyst, such as alumina, etc., thereby reducing the peroxide value are more preferred.

In the furfural composition and the production method of a furan compound according to the present invention, a concentration of 2-acetylfuran contained in the furfural composition is preferably 120 ppm by weight or more and 1,000 ppm by weight or less. When this 2-acetylfuran concentration is too high, there is a concern that in producing a furan compound using the furfural composition as a raw material through the decarbonylation reaction, the yield of the desired furan compound is lowered, and the purity of the obtained furan compound is lowered, too. Meanwhile, when this 2-acetylfuran concentration is too low, there is also a concern that in producing a furan compound using the furfural composition as a raw material through the decarbonylation reaction, the yield of the desired furan compound is lowered.

In the furfural composition and the production method of a furan compound according to the present invention, the concentration of 2-acetylfuran contained in the furfural composition is preferably 120 ppm by weight or more, more preferably 150 ppm by weight or more, still more preferably 200 ppm by weight or more, and especially preferably 250 ppm by weight or more. Meanwhile, this concentration is preferably 1,000 ppm by weight or less, more preferably 600 ppm by weight or less, and still more preferably 350 ppm by weight or less.

Although a reason why the 2-acetylfuran concentration in the furfural composition influences the yield of the furan compound obtained through the decarbonylation reaction of the furfural compound is not always elucidated yet, the following reasons may be conjectured. Namely, it may be considered that in the decarbonylation reaction of the furfural compound, the 2-acetylfuran in the furfural composition as a raw material is liable to bond to a catalyst metal species, etc. of the decarbonylation reaction catalyst and forms an acetyl-metal species, etc. on a catalyst carrier, and this acetyl-metal species inhibits the decarbonylation reaction of the furfural compound. It may be conjectured that the higher this concentration, the more increased the reaction inhibition is. In addition, it may be considered that the furfural compound is high in reactivity, the furfural compounds are polymerized each other on the catalyst, and the resulting polymer causes coking of the catalyst, thereby inhibiting the decarbonylation reaction. As for a polymerization mechanism, for example, in the case of furfural, it may be considered that there is a high possibility that the polymerization mainly occurs at the 5-position of the furan ring and the formyl group. Therefore, in view of the fact that the 2-acetylfuran appropriately exists, the extension of a polymer chain can be prevented. As a result, it may be estimated that when the concentration of 2-acetylfuran is too low, the coking of the catalyst cannot be inhibited, so that a lowering of the reaction yield occurs.

In the furfural composition and the production method of a furan compound according to the present invention, a method of controlling the 2-acetylfuran concentration in the furfural composition as a raw material is not particularly limited. However, examples thereof include a method of adding 2-acetylfuran; a method of converting 2-acetylfuran into a decarbonylated product, a hydrogenated product, or a polymerized product in the presence of a catalyst, thereby reducing the concentration of 2-acetylfuran; a method of subjecting a hydrogenated product of 2-acetylfuran to dehydrogenation in the presence of a catalyst, thereby increasing the 2-acetylfuran; a method of subjecting a polymer having a 2-acetylfuran structure to depolymerization in the presence of a catalyst, thereby increasing the 2-acetylfuran; a method of heating/decomposing 2-acetylfuran in the furfural composition, thereby reducing the concentration of 2-acetylfuran; a method of distilling the furfural composition to separate 2-acetylfuran, thereby reducing the concentration of 2-acetylfuran; a method of extracting and separating the furfural composition, thereby reducing the concentration of 2-acetylfuran; and the like. Among these, a method of undergoing distillation and separation is preferred.

As for a method of controlling the concentration of the compound containing nitrogen in the furfural composition, in addition to a method in which the furfural composition is distilled to separate the compound containing nitrogen, thereby reducing the concentration of the compound containing nitrogen, it is also possible to control the concentration of the compound containing nitrogen by the following methods. For example, a method of adsorbing the compound containing nitrogen with an adsorbent, thereby reducing the concentration of the compound containing nitrogen; a method of treating the compound containing nitrogen with a solid acid, thereby reducing the concentration of the compound containing nitrogen; a method of extracting and separating the furfural composition, thereby reducing the concentration of the compound containing nitrogen; a method of diluting the furfural composition with a furfural composition having low concentration of the compound containing nitrogen; a method of adding a compound containing nitrogen, thereby increasing the concentration of the compound containing nitrogen; a method of adding a furfural composition having high concentration of the compound containing nitrogen; and so on are also suitably adopted.

Each of the furfural composition and the furfural composition as a raw material in the production method of a furan compound according to the present invention is stored in a drum or a tank. As for a storage condition thereof, the furfural composition is preferably stored in an atmosphere in which an oxygen concentration of a gas phase part in the interior of a container for storage is 3% or less. The oxygen concentration is more preferably 1% or less, and still more preferably 0.1% or less. There is a concern that as this concentration becomes high, the peroxide value in the furfural composition increases during storing the furfural composition of the present invention. In order to control the oxygen concentration within the above-described range, the gas phase part in the container (drum or tank) for storing the furfural composition may be purged with an inert gas. As the inert gas, carbon dioxide, argon, nitrogen, helium, or the like is suitably used. Above all, it is more preferred to purge the gas phase part with nitrogen.

In addition, as for a temperature at the time of storage, the storage is performed with controlling the temperature to preferably 50° C. or lower, more preferably 40° C. or lower, and still more preferably an outside air temperature or lower. There is a concern that as this temperature becomes high, the concentration of the furfural dimer in the furfural composition increases during storing the furfural composition of the present invention.

<Furan Compound>

The furan compound which is obtained by the production method of a furan compound according to the present invention refers to compounds represented by the following general formulae (2) to (6).

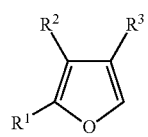

(2)

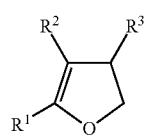

(3)

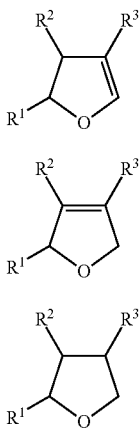

In the formulae (2) to (6), $R^1$, $R^2$, and $R^3$ are synonymous with those in the foregoing formula (1).

Specific examples of the furan compound according to the present invention include 2-methylfuran, 3-methylfuran, furan, 2,3-dihydrofuran, 2,5-dihydrofuran, furfuryl alcohol, tetrahydrofuran, 2-methyltetrahydrofuran, 3-methyltetrahydrofuran, tetrahydrofurfuryl alcohol, 2,5-dihydroxymethyl tetrahydrofuran, and the like, with furan being especially suitable.

In the production method of a furan compound according to the present invention, the obtained furan compound is obtainable through a decarbonylation reaction of the furfural composition as described later. Carbon monoxide and by-products which are by-produced by the reaction, an unreacted furfural compound, nitrogen, hydrogen, and so on are separated, and the resulting furan compound is then purified by an operation, such as distillation, etc. It is also possible for the separated carbon monoxide to be recycled as a carrier gas for a decarbonylation reaction as described later, effectively used for other applications, or burnt and subjected to heat recovery.

In the production method of furan compound according to the present invention, the obtained furan compound is extremely low in the content of impurities, and therefore, it is useful as various resin raw materials or additives. In addition, for the same reason, the obtained furan compound is useful as intermediates for derivative synthesis. For example, so far as the furan compound is the furan compound represented by the general formula (2), it can be converted into the furan compound represented by the general formula (6) through a hydrogenation reaction using a catalyst.

Specifically, the production method according to the present invention is useful for production of tetrahydrofuran from furan. Although a production method of tetrahydrofuran is not particularly limited so long as it is a conventionally known method, it is preferred to produce tetrahydrofuran from furan through a hydrogenation reaction using a catalyst having an element belonging to the Groups 8 to 10 of the long form of the periodic table (hereinafter referred to simply as "periodic table") supported on a carrier, such as active carbon, etc.

The furan obtained from the furfural composition according to the present invention can also be converted into, in addition to tetrahydrofuran, a diol, such as 1,4-butanediol, etc., or a lactone, such as γ-butyrolactone, γ-valerolactone, etc., through a combination with hydration or the like.

By using the furfural composition according to the present invention as a raw material for production of a furan compound, in producing tetrahydrofuran from furan, the concentration of 2-methyltetrahydrofuran formed from 2-acetylfuran is reduced, thereby enabling the purity of tetrahydrofuran to be increased. In addition, the furan can also be converted into a diol, such as 1,4-butanediol, etc., or a lactone, such as γ-butyrolactone, γ-valerolactone, etc., through a combination with hydration or the like.

<Decarbonylation Reaction>

Although the decarbonylation reaction in the production method of a furan compound according to the present invention may be any of a liquid phase or gas phase reaction, it is preferably a gas phase reaction. The reaction mode of the decarbonylation reaction is not particularly prescribed, and it can be carried out by any of a batch reaction or a continuous flow reaction. However, it is preferred to use a continuous flow reaction mode from the industrial standpoint. In the case of a gas phase flow reaction, typically, a gas of the furfural composition containing, as a main component, the above-described furfural compound is continuously fed as a raw material into a tubular reactor filled with a catalyst and allowed to pass through the catalyst within the reactor to advance the reaction, thereby obtaining the furan compound. It is preferred that the furfural composition containing, as a main component, the furfural compound is previously gasified in a vaporizer as provided. Although the gasification method is not particularly limited, examples thereof include a method in which the furfural composition containing, as a main component, the furfural compound in a liquid state is subjected to gas bubbling with hydrogen, an inert gas, or the like; a method of gasifying the furfural composition by means of spray gasification; and the like.

A moisture concentration in the furfural composition as a raw material to be subjected to the decarbonylation reaction is preferably 10 ppm by weight or more and 1% by weight or less, more preferably 15 ppm by weight or more and 1,000 ppm by weight or less, and still more preferably 20 ppm by weight or more and 500 ppm by weight or less. When the moisture concentration is too high, the yield is lowered, whereas when it is too low, a raw material purification load becomes large. In the decarbonylation reaction of the furfural compound, it is suitable to allow hydrogen to coexist as a reaction initiator. Although a feed amount of the furfural composition containing, as a main component, the furfural compound is not particularly limited, it is typically 0.0001 mol/h or more and 50,000 mol/h or less, preferably 0.001 mol/h or more and 10,000 mol/h or less, and more preferably 0.01 mol/h or more and 5,000 mol/h or less per mol of a noble metal bearing the catalytic activity.

In the case of a gas phase flow reaction, although a retention time thereof is not particularly limited, it is typically 0.001 seconds or more and 10 seconds or less, preferably 0.01 seconds or more and 5 seconds or less, more preferably 0.05 seconds or more and 2 seconds or less, and especially preferably 0.1 seconds or more and 1 second or less.

Although a reaction temperature is not particularly limited, in general, it is preferably 170° C. or higher and 450° C. or lower, more preferably 180° C. or higher and 380° C. or lower, still more preferably 200° C. or higher and 340° C. or lower, and especially preferably 230° C. or higher and 300° C. or lower. When the reaction temperature is too low, the furfural compound is hard to be sufficiently converted, whereas when the reaction temperature is too high, the formed furan compound causes a successive reaction, and as a result, there is a tendency that the yield of the furan compound is lowered.

Although a reaction pressure is not particularly limited, it is typically 0.01 MPa or more and 3 MPa or less, preferably 0.05 MPa or more and 2 MPa or less, and more preferably 0.1 MPa or more and 1 MPa or less in terms of an absolute pressure.

Although a catalyst that is used for the decarbonylation reaction is not particularly limited, a solid catalyst is preferably used. As a catalyst metal of the solid catalyst, at least one metal selected from transition metal elements belonging to the Groups 8 to 10 of the periodic table is suitably used. As the transition metal elements belonging to the Groups 8 to 10 of the periodic table, Ni, Ru, Ir, Pd, and Pt are preferred; Ru, Ir, Pd, and Pt are more preferred; Pd and Pt are still more preferred. Above all, Pd whose selectivity for conversion of furfural into furan is extremely high is especially preferred.

Although the kind of a carrier is not particularly limited, carriers of single metal oxides, such as $Al_2O_3$, $SiO_2$, $TiO_2$, $ZrO_2$, MgO, etc., and complex metal oxides thereof, porous oxides, such as zeolite, etc., and active carbon can be used. In order to improve the performance of the catalyst, such a supported metal catalyst can contain a modification assistant. Examples of the modification assistant include the Group 1 metals and ions thereof, the Group 2 metals and ions thereof, the Group 4 metals and ions thereof, and the Group 6 metals and ions thereof, of the periodic table, wherein the Group 1 metals and ions thereof are preferred.

EXAMPLES

Although the present invention is hereunder described in more detail with reference to Examples, it should be construed that the present invention is not limited by the following Examples so long as the gist of the present invention is not deviated. It is to be noted that in the following Examples, the analysis of moisture was performed by the Karl Fischer method (measurement apparatus: CA-21, manufactured by Mitsubishi Chemical Corporation). The analysis of each of furfural and a furfural dimer was performed by means of gas chromatography and calculated in terms of an area percentage. It is to be noted that a value resulting from subtraction of a moisture concentration from 100% by weight was calculated, and the remaining weight percent was calculated in terms of an area percentage of each component of the gas chromatography. It is to be noted that the furfural dimer concentration was the total of 5-(2-furanylcarbonyl)-2-furancarboxyaldehyde and bis-2-furylethanedione. The analysis of 2-acetylfuran was performed by means of gas chromatography and calculated in terms of an area percentage. The peroxide value was determined by the potassium addition redox titration in a nitrogen atmosphere (iodometry), and a potentiometric titrator (Titrando 808, manufactured by Metrohm Ltd.), a composite platinum electrode (manufactured by Metrohm, #6.0401.100, 3N KCl internal reference electrode electrolytic solution), and a titration agent (0.005N $Na_2SO_3$ aqueous solution) were used.

Production Example 1

[Production of Furfural Composition]

A glass-made chromatographic tube having a capacity of 100 cc and equipped with a jacket capable of being heated by circulating warm water was filled with 70 cc of an anion exchange resin ("DIAION" (a registered trademark), manufactured by Mitsubishi Chemical Corporation, model name: WA20), and furfural (purity: 98.7% by weight), manufactured by Kanematsu Chemicals Corporation was circulated at a rate of 140 cc/h into this glass-made chromatographic tube. On that occasion, a contact temperature between the anion exchange resin and the furfural was 40° C., and a pressure was atmospheric pressure.

In the present Production Example, an operation of removing a high-boiling component from the furfural having been subjected to the treatment with the anion exchange resin is subsequently carried out. As a distillation column for performing the distillation of the foregoing liquid, an Oldershaw distillation column with 30 plates (number of theoretical plate: 20 plates) was used. The raw material furfural was continuously introduced at a flow rate of 90 cc/hr into a position of the 15th plate from the column bottom at a column top pressure of 6.7 kPa, a column bottom temperature of 98° C., and a reflux ratio of 1.0, and continuous distillation from the column top part was performed at a rate of 81 cc/hr, whereas continuous discharge from the column bottom was performed at a rate of 9 cc/hr. According to the present continuous distillation, a furfural liquid (column top distillate) having a composition such that the furfural purity was 99.95%, and a sum total of light-boiling components was 0.03% was obtained from the column top. It is to be noted that an oil bath was used as a heat source of the distillation, and a temperature of the oil bath was set to 131° C.

In order to perform an operation for removing the light-boiling component in the obtained column top distillate, an Oldershaw distillation column with 25 plates (number of theoretical plate: 15 plates) was used. The column top distillate was continuously introduced at a flow rate of 100 cc/hr into a position of the 10th plate from the column bottom at a column top pressure of 33.3 kPa, a column bottom temperature of 130° C., and a reflux ratio of 50; continuous distillation from the column top part was performed at a rate of 1 cc/hr; continuous discharge from the column bottom was performed at a rate of 2 cc/hr; and sidestream discharge from a position of the 13th plate from the column bottom was performed at a rate of 97 cc/hr. According to the present continuous distillation, the obtained sidestream discharge liquid was obtained in such a composition that the furfural purity was 99.97%, the furfural dimer content was not more than a detection limit, the peroxide value was 0.32 mEq/kg, and the nitrogen compound concentration was 2.0 ppm by weight in terms of a nitrogen atom. The acetylfuran concentration was 293 ppm by weight. It is to be noted that an oil bath was used as a heat source of the distillation, and a temperature of the oil bath was set to 175° C.

Production Example 2

[Production of Furfural Composition]

The same procedures as in Production Example 1 were all carried out, except for performing the distillation for separating the light-boiling component by means of continuous distillation from the column top part at a rate of 1 cc/hr and performing the continuous discharge from the column bottom at a rate of 99 cc/hr. It is to be noted that an oil bath was used as a heat source of the distillation, and a temperature of the oil bath was set to 145° C. According to the present continuous distillation, the obtained bottom discharge liquid was obtained in such a composition that the furfural purity was 99.78%, the furfural dimer content was 0.03% by weight, the peroxide value was 1.03 mEq/kg, and the nitrogen compound concentration was 1.3 ppm by weight in terms of a nitrogen atom.

Production Example 3

[Production of Furfural Composition]

With respect to the furfural composition obtained in Production Example 2, an Oldershaw distillation column with 10 plates (number of theoretical plate: 5 plates) was used. The raw material furfural was continuously introduced at a flow rate of 90 cc/hr into a position of the 5th plate from the column bottom at a column top pressure of 6.7 kPa, a column bottom temperature of 98° C., and a reflux ratio of 1.0, and continuous distillation from the column top part was performed at a rate of 89 cc/hr, whereas continuous discharge from the column bottom was performed at a rate of 1 cc/hr. According to the present continuous distillation, the furfural liquid from the column top (column top distillate) was obtained from the column top in such a composition that the furfural purity was 99.94%, the furfural dimer content was not more than a detection limit, the peroxide value was 0.57 mEq/kg, and the nitrogen compound concentration was 1.3 ppm by weight in terms of a nitrogen atom.

Production Example 4

[Production of Furfural Composition]

In Production Example 1, the distillation was carried out in such a manner that the air leakage of the distillation column was less than 1.3 kPa/hr. According to the present continuous distillation, the furfural liquid from the column top (column top distillate) was obtained from the column top in such a composition that the furfural purity was 99.97%, the furfural dimer content was 0.05 ppm by weight, the peroxide value was 0.19 mEq/kg, and the nitrogen compound concentration was 2.0 ppm by weight in terms of a nitrogen atom.

Production Example 5

[Production of Furfural Composition]

A 500-L SUS304-made pot was filled with 35 kg of an anion exchange resin ("DIAION" (a registered trademark), manufactured by Mitsubishi Chemical Corporation, model name: WA20), and 100 kg of furfural (purity: 98.7% by weight), manufactured by Kanematsu Chemicals Corporation was filled in this pot. Thereafter, the contents were stirred at 40° C. for 30 minutes, and the liquid and the resin were separated from each other by a filter. The pressure was atmospheric pressure. Thereafter, the liquid was again filled in the pot, 35 kg of the anion exchange resin after washing was filled, and the contents were stirred at 40° C. for 30 minutes. These operations were repeated until the moisture of the liquid reached 200 ppm by weight or less.

In the present Production Example, an operation of removing a high-boiling component from the furfural having been subjected to the treatment with the anion exchange resin is subsequently carried out. As a distillation column for performing the distillation of the foregoing liquid, a distillation column having the number of theoretical plate of 20 plates was used. The raw material furfural was continuously introduced at a flow rate of 30 L/hr into a position of the 15th plate from the column bottom at a column top pressure of 6.7 kPa, a column bottom temperature of 98° C., and a reflux ratio of 1.0, and continuous distillation from the column top part was performed at a rate of 27 L/hr, whereas continuous discharge from the column bottom was performed at a rate of 3 L/hr. According to the present continuous distillation, a furfural liquid (column top distillate) having a composition such that the furfural purity was 99.95%, and a sum total of light-boiling components was 0.03% was obtained from the column top. It is to be noted that steam was used as a heat source of the distillation, and a steam temperature was set to 130° C.

In order to perform an operation for removing the light-boiling component in the obtained column top distillate, a packed column having the number of theoretical plate of 23 plates was used. The column top distillate was continuously introduced at a flow rate of 50 L/hr into a position of the 5th plate from the column bottom at a column top pressure of 33.3 kPa, a column bottom temperature of 120° C., and a reflux ratio of 100; continuous distillation from the column top part was performed at a rate of 0.5 L/hr; continuous discharge from the column bottom was performed at a rate of 1 L/hr; and sidestream discharge from a position of the 13th plate from the column bottom was performed at a rate of 48.5 L/hr. According to the present continuous distillation, the obtained sidestream discharge liquid was obtained in such a composition that the furfural purity was 99.97%; the furfural dimer content was not more than a detection limit; the peroxide value was 0.12 mEq/kg; the acetylfuran concentration was 200 ppm by weight; and the nitrogen compound concentration was 2.0 ppm by weight in terms of a nitrogen atom.

Example 1

[Production of Furan Compound by Decarbonylation Reaction of Furfural Composition]

In an SUS-made reaction tube having an inside diameter of 13.4 mm, 12.0 g of a supported Pd catalyst (1% by weight Pd-1% by weight K/$ZrO_2$) which had been crushed to a size of 0.6 mm or less was filled, and the temperature of the catalyst was increased to 231° C. under circulation of 22.5 mmol/h of hydrogen and 292.5 mmol/h of nitrogen. The furfural composition purified in Production Example 1 was allowed to pass through a vaporizer heated at 245° C. and vaporized, followed by feeding at a flow rate of 362.2 mmol/h, to commence a decarbonylation reaction. At that time, a hydrogen/furfural ratio was 0.05. A reaction pressure was 0.4 MPa in terms of an absolute pressure.

A part of the reaction gas obtained from an outlet of the reaction tube was introduced into a gas chromatograph (GC), thereby quantitating the furan compound, carbon monoxide, nitrogen, and other products.

For the gas chromatographic analysis of inorganic gases, such as carbon monoxide, nitrogen, etc., a thermal conductivity detector was used as a detector, and a packed column filled with Molecular Sieve 13X (a trade name, manufactured by GL Sciences Inc., mesh 60/80) and having a column length of 3 m was used as a column. It is to be noted that the analysis was carried out by setting a temperature of each of the sample introducing part and the detection part to 90° C., a temperature of the column to 70° C., and a current value to be flown into the detection part to 70 mA, respectively.

For the gas chromatographic analysis of organic gases, such as furfural, furan, etc., a thermal conductivity detector was used as a detector, and a packed column filled with Thermon-1000 (a trade name, manufactured by GL Sciences Inc., medium polarity) and having a column length of 3 m was used as a column. It is to be noted that the analysis was carried out in such a manner that a temperature of the sample introducing part was set to 200° C.; a temperature of the detection part was set to 220° C.; a column temperature was increased at a rate of 3° C./min from 80° C. to 110° C.; after reaching 110° C., the temperature was increased to 225° C. at a rate of 5° C./min; after reaching 225° C., the temperature was kept for 17 minutes; and a current value to be flown into the detection part was set to 80 mA.

It is to be noted that a conversion of the furfural compound (furfural conversion) (%) and a selectivity of the furan compound (furan selectivity) (%) were calculated according to the following equations.

Furfural conversion (%)=[1−{(Residual amount of furfural compound after reaction (mol))/(Feed amount of furfural compound (mol))}]×100

Furan selectivity (%)=[{(Yield of furan compound (%))/(Conversion of furfural compound (%))}×100=[{(Formation amount of furan compound (mol))/(Feed amount of furfural compound (mol))}×100/(Furfural conversion (%))]×100

As a result of performing the decarbonylation reaction under the above-described condition, 60 hours after commencing the reaction, the furfural conversion was 99.64%, and the furan selectivity was 99.64%. The results are shown in Table 1.

Example 2

The production of a furan compound through the decarbonylation reaction was carried out under exactly the same conditions as in Example 1, except for changing the furfural composition as a raw material from the furfural composition of Production Example 1 to the furfural composition of Production Example 3. 60 hours after commencing the reaction, the furfural conversion was 99.35%, and the furan selectivity was 99.51%. The results are shown in Table 1.

Example 3

The production of a furan compound through the decarbonylation reaction was carried out under exactly the same conditions as in Example 1, except for changing the furfural composition as a raw material from the furfural composition of Production Example 1 to the furfural composition of Production Example 4. The furfural conversion was 99.38%, and the furan selectivity was 98.61%, at 60 hours after commencing the reaction. The results are shown in Table 1.

Comparative Example 1

The production of a furan compound through the decarbonylation reaction was carried out under exactly the same conditions as in Example 1, except for changing the furfural composition as a raw material from the furfural composition of Production Example 1 to the furfural composition of Production Example 2. The furfural conversion was 97.35%, and the furan selectivity was 97.73%, at 60 hours after commencing the reaction. The results are shown in Table 1.

Example 4

After mixing 5.0 g of the furfural composition of Production Example 5 and 1.0 g of a supported Pd catalyst (1% by weight Pd-1% by weight K/ZrO$_2$) which had been crushed to a size of 0.6 mm or less, those are filled in a 200-mL autoclave. After purging the autoclave with nitrogen three times, the autoclave was evacuated, and 58 cc of hydrogen was then injected. Nitrogen was charged in the autoclave to set the pressure to 0.4 MPa, and a liquid phase decarbonylation reaction was carried out at an internal temperature of the autoclave of 200° C. for 5 hours. The reaction mixture was cooled and then taken out, followed by gas chromatographic analysis. As a result, the furfural conversion was 79.96%, and the furan selectivity was 99.86%. The results are shown in Table 1.

Example 5

The production of a furan compound through the decarbonylation reaction was carried out under exactly the same conditions as in Example 4, except for changing the furfural composition as a raw material from the furfural composition of Production Example 5 to the furfural composition of Production Example 1. The furfural conversion was 77.55%, and the furan selectivity was 99.85%, at 5 hours after commencing the reaction. The results are shown in Table 1.

Example 6

The production of a furan compound through the decarbonylation reaction was carried out under exactly the same conditions as in Example 5, except for changing the furfural composition as a raw material from the furfural composition of Production Example 1 to the furfural composition of Production Example 4. The furfural conversion was 74.61%, and the furan selectivity was 99.75%, at 5 hours after commencing the reaction. The results are shown in Table 1.

Comparative Example 2

The production of a furan compound through the decarbonylation reaction was carried out under exactly the same conditions as in Example 5, except for changing the furfural composition as a raw material from the furfural composition of Production Example 1 to the furfural composition of Production Example 2. The furfural conversion was 70.71%, and the furan selectivity was 99.59%, at 5 hours after commencing the reaction. The results are shown in Table 1.

Comparative Example 3

The production of a furan compound through the decarbonylation reaction was carried out under exactly the same conditions as in Example 5, except for changing the furfural composition as a raw material from the furfural composition of Production Example 1 to a furfural composition resulting from mixing the furfural composition of Production Example 1 with the bottom liquid obtained by light-boiling separation distillation of Production Example 1 in a weight ratio of 97/2. At 5 hours after commencing the reaction, the furfural conversion was 67.47%, and the furan selectivity was 99.64%. The results are shown in Table 1.

Comparative Example 4

The production of a furan compound through the decarbonylation reaction was carried out under exactly the same conditions as in Example 5, except for changing the furfural composition as a raw material from the furfural composition of Production Example 1 to a furfural composition resulting from mixing the furfural composition of Production Example 2 with bis-2-furylethanedione (manufactured by Aldrich, purity: 98%) such that the furfural dimer concentration was 0.11% by weight. At 5 hours after commencing the reaction, the furfural conversion was 66.72%, and the furan selectivity was 99.75%. The results are shown in Table 1.

Production Example 6

[Production of Furfural Composition]

A glass-made chromatographic tube having a capacity of 100 cc and equipped with a jacket capable of being heated by circulating warm water was filled with 70 cc of an anion exchange resin ("DIAION" (a registered trademark), manufactured by Mitsubishi Chemical Corporation, model name: WA20), and furfural (purity: 98.7% by weight), manufactured by Kanematsu Chemicals Corporation was circulated at a rate of 140 cc/h into this glass-made chromatographic tube. On that occasion, a contact temperature between the anion exchange resin and the furfural was 40° C., and a pressure was atmospheric pressure.

Using an Oldershaw distillation column having a column diameter of 35 mm and the number of theoretical plate of 5 plates, 1,000.0 g of the obtained furfural was distilled at a column top pressure of 13.3 kPa and a column bottom temperature of 102° C.

TABLE 1

|  | Furfural composition | | | Decarbonylation reaction | | |
| --- | --- | --- | --- | --- | --- | --- |
|  | Concentration of the compound containing nitrogen [ppm by mass] | Furfural dimer concentration [ppm by mass] | Peroxide value [mEq/kg] | Gas phase/ Liquid phase | Furfural conversion [%] | Furan selectivity [%] |
| Example 1 | 2 | ND | 0.32 | Gas phase | 99.64 | 99.64 |
| Example 2 | 1.3 | ND | 0.57 | Gas phase | 99.35 | 99.51 |
| Example 3 | 2 | 500 | 0.19 | Gas phase | 99.38 | 98.61 |
| Comparative Example 1 | 1.3 | 300 | 1.03 | Gas phase | 97.35 | 97.73 |
| Example 4 | 2 | ND | 0.12 | Liquid phase | 79.96 | 99.86 |
| Example 5 | 2 | ND | 0.32 | Liquid phase | 77.55 | 99.85 |
| Example 6 | 2 | 500 | 0.19 | Liquid phase | 74.61 | 99.75 |
| Comparative Example 2 | 1.3 | 300 | 1.03 | Liquid phase | 70.71 | 99.59 |
| Comparative Example 3 | 3 | 200 | 1.35 | Liquid phase | 67.47 | 99.64 |
| Comparative Example 4 | 1.3 | 1100 | 1.03 | Liquid phase | 66.72 | 99.75 |

ND: Not more than a detection limit

The following may be said from Table 1. Namely, in comparison of the results regarding the conversion of the furfural compound and the selectivity of the furan compound in the decarbonylation reaction of Examples 1 to 6 and Comparative Examples 1 to 4, it is noted that in all of the gas phase reaction and the liquid phase reaction, when a furfural composition in which each of the furfural dimer concentration and the peroxide value falls within a specified range is used as the raw material for production of a furan compound, the furfural composition becomes useful as the raw material for industrial production of a furan compound since the composition is high in both the conversion and the selectivity.

An oil bath was used as a heat source of the distillation, and a temperature of the oil bath was set to 120° C. A distillate was discharged successively from an initial distillate containing a lot of a light-boiling component, thereby acquiring furfural compositions Fr-1 to Fr-6, respectively. It is to be noted that Fr-1 to Fr-6 are distillates discharged 1 hour, 2 hours, 3 hours, 4.2 hours, 5.5 hours, and 7.2 hours, respectively after commencing the distillation.

Then, when the distillation reached a proportion of 90% by weight relative to the furfural in the column bottom liquid of the distillation column, the distillation was terminated. Concentrations of the furfural of each of Fr-1 to Fr-6 and the 2-acetylfuran are shown in the following Table 2.

TABLE 2

| Production Example 6 | | Fr-1 | Fr-2 | Fr-3 | Fr-4 | Fr-5 | Fr-6 |
| --- | --- | --- | --- | --- | --- | --- | --- |
| Raw material furfural composition | Furfural purity [% by weight] | 99.26 | 99.85 | 99.53 | 99.77 | 99.68 | 95.64 |
|  | 2-Acetylfuran content [ppm by weight] | 359 | 532 | 922 | 1343 | 2255 | 4624 |

Production Example 7

[Production of Furfural Composition]

Furfural compositions Fr-1 to Fr-6 were produced under exactly the same conditions as in Production Example 6, except for using an Oldershaw distillation column having the number of theoretical plate of 20 plates. Fr-1 to Fr-6 are distillates discharged 1 hour, 2 hours, 3 hours, 4.2 hours, 5.5 hours, and 7.2 hours, respectively after commencing the distillation.

Concentrations of the furfural of each of Fr-1 to Fr-6 and the 2-acetylfuran are shown in the following Table 3.

TABLE 3

| Production Example 7 | | Fr-1 | Fr-2 | Fr-3 | Fr-4 | Fr-5 | Fr-6 |
|---|---|---|---|---|---|---|---|
| Raw material furfural composition | Furfural purity [% by weight] | 98.35 | 99.96 | 99.92 | 99.72 | 99.55 | 99.21 |
| | 2-Acetylfuran content [ppm by weight] | 40 | 110 | 293 | 341 | 789 | 1357 |

Example 7

[Production of Furan Compound by Decarbonylation Reaction of Furfural Composition]

In a glass-type reaction tube having an inside diameter of 6 mm, 0.75 g of a supported Pd catalyst (1% by weight Pd-1% by weight K/ZrO$_2$) which had been crushed to a size of 0.6 mm or less was filled, and the temperature of the catalyst was increased to 231° C. under circulation of 2.25 mmol/h of hydrogen and 85.71 mmol/h of nitrogen. The furfural composition (Fr-2) purified in Production Example 6 was allowed to pass through a vaporizer heated at 182° C. and vaporized, followed by feeding at a flow rate of 36.22 mmol/h, to commence a decarbonylation reaction. At that time, a hydrogen/furfural compound ratio was 0.062. A reaction pressure was 0.1 MPa in terms of an absolute pressure.

A part of the reaction gas obtained from an outlet of the reaction tube was introduced into a gas chromatograph, thereby quantitating the furan compound, carbon monoxide, nitrogen, and other products.

As a result of performing the decarbonylation reaction under the above-described condition, 12 hours after commencing the reaction, the furfural conversion was 99.5%, and the furan selectivity was 93.5%. The results are shown in Table 4.

Example 8

The production of a furan compound through the decarbonylation reaction was carried out under exactly the same conditions as in Example 7, except for changing the furfural composition as a raw material from Fr-2 of Production Example 6 to Fr-3 of Production Example 6. At 12 hours after commencing the reaction, the furfural conversion was 97.7%, and the furan selectivity was 94.1%. The results are shown in Table 4.

Example 9

The decarbonylation reaction was carried out under exactly the same conditions as in Example 7, except for changing the furfural composition as a raw material from Fr-2 of Production Example 6 to Fr-3 of Production Example 7. At 12 hours after commencing the reaction, the furfural conversion was 99.5%, and the furan selectivity was 99.5%. The results are shown in Table 4.

Comparative Example 5

The production of a furan compound through the decarbonylation reaction was carried out under exactly the same conditions as in Example 7, except for changing the furfural composition as a raw material from Fr-2 of Production Example 6 to Fr-6 of Production Example 6. At 12 hours after commencing the reaction, the furfural conversion was 90.9%, and the furan selectivity was 93.5%. The results are shown in Table 4.

Comparative Example 6

The decarbonylation reaction was carried out under exactly the same conditions as in Example 9, except for changing the furfural composition as a raw material from Fr-3 of Production Example 7 to Fr-2 of Production Example 7. At 12 hours after commencing the reaction, the furfural conversion was 88.3%, and the furan selectivity was 99.3%. The results are shown in Table 4.

Comparative Example 7

The production of a furan compound through the decarbonylation reaction was carried out under exactly the same conditions as in Example 7, except for changing the furfural composition as a raw material from Fr-2 of Production Example 6 to Fr-4 of Production Example 6. At 12 hours after commencing the reaction, the furfural conversion was 98.6%, and the furan selectivity was 92.8%. The results are shown in Table 4.

Comparative Example 8

The production of a furan compound through the decarbonylation reaction was carried out under exactly the same conditions as in Example 7, except for changing the furfural composition as a raw material from Fr-2 of Production Example 6 to purchased furfural (manufactured by Kanematsu Chemicals Corporation). At 12 hours after commencing the reaction, the furfural conversion was 85.6%, and the furan selectivity was 92.5%. The results are shown in Table 4.

TABLE 4

|  |  | Example 7 | Example 8 | Example 9 | Comparative Example 5 | Comparative Example 6 | Comparative Example 7 | Comparative Example 8 |
|---|---|---|---|---|---|---|---|---|
| Raw material furfural composition | Furfural purity (% by weight) | 99.85 | 99.53 | 99.92 | 95.64 | 99.96 | 99.77 | 99.77 |
|  | 2-Acetylfuran content (ppm by weight) | 532 | 922 | 293 | 4624 | 110 | 1343 | 1245 |
|  | Moisture concentration (ppm by weight) | 280 | 255 | 385 | 310 | 224 | 270 | 1235 |
|  | Furfural dimer concentration (ppm by weight) | ND | ND | ND | ND | ND | ND | ND |
|  | Peroxide value (mEq/kg) | 0.78 | 0.65 | 0.35 | 1.35 | 0.59 | 0.57 | 1.24 |
| Reaction results | Furfural conversion (%) | 99.5 | 97.7 | 99.5 | 90.9 | 88.3 | 98.6 | 85.6 |
|  | Furan selectivity (%) | 93.5 | 94.1 | 99.5 | 93.5 | 99.3 | 92.8 | 92.5 |
|  | Furan yield (%) | 93.0 | 91.9 | 99.0 | 85.0 | 87.7 | 91.5 | 79.2 |

From the decarbonylation reaction results of Examples 7 to 9 and Comparative Examples 5, 7, and 9, it is noted that the lower the 2-acetylfuran concentration, the higher the furan yield is.

Meanwhile, from the results of Examples 7 to 9 and Comparative Example 6, it is noted that when the 2-acetylfuran concentration is too low, the furan yield is lowered.

While the invention has been described in detail and with reference to specific embodiments thereof, it will be apparent to one skilled in the art that various changes and modifications can be made therein without departing from the spirit and scope thereof. It is to be noted that the present application is based on a Japanese patent application filed on Mar. 27, 2015 (Japanese Patent Application No. 2015-067199), and the contents are incorporated herein by reference.

The invention claimed is:

1. A furfural composition having
 a concentration of a furfural compound of 99.00% by weight to 99.97% by weight,
 a concentration of a furfural dimer of 1,000 ppm by weight or less, and
 a peroxide value of 0.01 mEq/kg or more and 0.90 mEq/kg or less.

2. The furfural composition according to claim 1, wherein a concentration of a 2-acetylfuran in the furfural composition is 120 ppm by weight or more and 1,000 ppm by weight or less.

3. The furfural composition according to claim 1, wherein a concentration of a compound containing nitrogen in the furfural composition is 0.1 ppm by weight or more and 50 ppm by weight or less in terms of a nitrogen atom.

4. The furfural composition according to claim 2, wherein a concentration of a compound containing nitrogen in the furfural composition is 0.1 ppm by weight or more and 50 ppm by weight or less in terms of a nitrogen atom.

* * * * *